(12) United States Patent
MacDonald et al.

(10) Patent No.: US 7,705,159 B2
(45) Date of Patent: Apr. 27, 2010

(54) PROCESS FOR THE PREPARATION OF LETROZOLE

(75) Inventors: Peter Lindsay MacDonald, Gentilino (CH); Ettore Bigatti, Balerna (CH); Pierluigi Rossetto, Balerna (CH); Zvi Harel, Kfar Saba (IL)

(73) Assignee: Sicor, Inc., Irvine, CA (US)

( * ) Notice: Subject to any disclaimer, the term of this patent is extended or adjusted under 35 U.S.C. 154(b) by 797 days.

(21) Appl. No.: 11/482,228

(22) Filed: Jul. 6, 2006

(65) Prior Publication Data

US 2007/0066831 A1    Mar. 22, 2007

Related U.S. Application Data

(60) Provisional application No. 60/697,217, filed on Jul. 6, 2005.

(51) Int. Cl.
*C07D 249/08*    (2006.01)
(52) U.S. Cl. .................................... 548/262.2; 514/383
(58) Field of Classification Search ................. 514/383; 548/262.2
See application file for complete search history.

(56) References Cited

U.S. PATENT DOCUMENTS

| | | | |
|---|---|---|---|
| 4,978,672 A | 12/1990 | Bowman et al. | |
| 5,280,035 A | 1/1994 | Bohlmann et al. | |
| 5,352,795 A | 10/1994 | Bowman et al. | |
| 5,473,078 A * | 12/1995 | Bowman et al. | ......... 548/262.2 |
| 2005/0209294 A1 | 9/2005 | Wadhwa et al. | |
| 2006/0128775 A1 | 6/2006 | Patel et al. | |
| 2007/0066831 A1 | 3/2007 | MacDonald et al. | |
| 2007/0100149 A1 | 5/2007 | Palle et al. | |
| 2007/0112202 A1 | 5/2007 | Friedman et al. | |
| 2007/0112203 A1 | 5/2007 | Hasson et al. | |
| 2007/0259935 A1 | 11/2007 | Westheim | |

FOREIGN PATENT DOCUMENTS

| | | |
|---|---|---|
| WO | WO 2004/076409 | 9/2004 |
| WO | WO 2005/047269 | 5/2005 |
| WO | WO-2007-039912 A1 | 4/2007 |
| WO | WO-2007/054964 A2 | 5/2007 |
| WO | WO-2007/074474 A1 | 7/2007 |
| WO | WO-2007/090464 A1 | 8/2007 |
| WO | WO-2007/107733 A1 | 9/2007 |
| WO | WO-2007/144896 A1 | 12/2007 |
| WO | WO-2008/090565 A1 | 7/2008 |

OTHER PUBLICATIONS

J. John et al. "Synthesis and Antimicrobial Activity of 2,4-Disubstituted Thiazole Derivatives Containing 1,2,4-Triazole Ring System" *Indian Journal of Heterocyclic Chemistry*, vol. 10, p. 295-298 (2001).
USP Official Monographs, vol. 28, p. 1112-1113 (2005).

* cited by examiner

*Primary Examiner*—Golam M. M. Shameem
*Assistant Examiner*—Susannah Chung
(74) *Attorney, Agent, or Firm*—Kenyon & Kenyon LLP

(57) ABSTRACT

The invention provides a high-yield process for the preparation of letrozole having a high purity, without the need for removal of the 4-[1-(1,3,4-triazolyl)methyl]benzonitrile impurity at the intermediate stage. The invention also provides a process for the synthesis of letrozole in which formation of the impurity 4-[1-(1,3,4-triazolyl)methyl]benzonitrile during the first stage is minimized. In the process, a 4-(halomethyl)benzonitrile is reacted with a salt of 1H-1,2,4-triazole, reducing the formation of the impurity. Preferably, the preparation is conducted as a one-pot process.

38 Claims, No Drawings

PROCESS FOR THE PREPARATION OF LETROZOLE

CROSS-REFERENCE TO RELATED APPLICATIONS

This application claims the benefit of U.S. provisional application Ser. No. 60/697,217, filed Jul. 6, 2005, the contents of which are incorporated herein by reference in their entirety.

FIELD OF THE INVENTION

The present invention is directed to an improved process for the preparation of letrozole and intermediates thereof.

BACKGROUND OF THE INVENTION

Letrozole, 4,4'-(1H-1,2,4-triazol-1-ylmethylene)bisbenzonitrile, which has the chemical structure

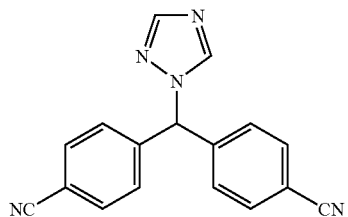

is an aromatase inhibitor, used for the first line treatment of advanced breast cancer in postmenopausal women with disease progression following antiestrogen therapy, and has been approved in the United States for postmenopausal women who have finished five years of treatment with Tamoxifen. As with other aromatase inhibitors, letrozole inhibits the action of the enzyme aromatase in the formation of estrogen.

U.S. Pat. No. 4,978,672 ("'672 patent") describes the synthesis of letrozole by reacting 4-(bromomethyl)benzonitrile I—Br

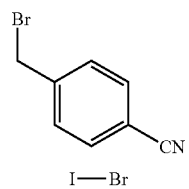

I—Br and 1H-1,2,4-triazole II

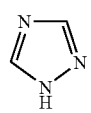

II to provide 4-[1-(1,2,4-triazolyl)methyl]benzonitrile III,

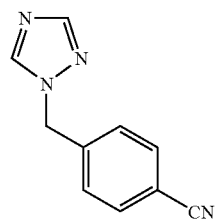

III which is then purified by column chromatography, and subsequently converted to letrozole by reaction with 4-fluorobenzoacetonitrile V

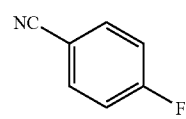

V

According to International Publication No. WO 2004/076409 ("WO '409"), compound III is purified by column chromatography in the '672 patent before conversion to letrozole, because it is contaminated with 4-[1-(1,3,4-triazolyl)methyl]benzonitrile IV,

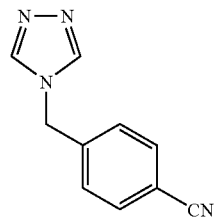

IV

WO '409 discloses that compound III is contaminated with approximately 20 to 40% of compound IV. WO '409 further recites that when the reaction of compound III with compound V is performed without the removal of the impurity (compound IV), the impurity is converted into 4,4'-(1H-1,3,4-triazol-1-ylmethylene)bisbenzonitrile VI,

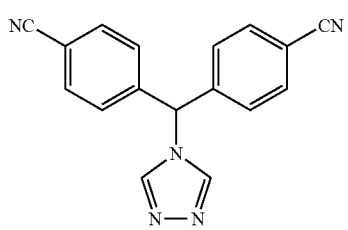

VI also known as letrozole related compound A, which is restricted to 0.3% by the USP *Official Monographs*, 28, 1112-1113 (2005). This need for purification of compound III makes the process of the '672 patent tedious, as well as unattractive commercially.

WO '409 describes an alternative process, which avoids the formation of compound IV by using an amino substituted triazole. However, this process requires an additional step to remove the amino substituent, which may involve the formation of dangerous diazo intermediates. Thus, the process is also undesirable for use on a commercial scale.

U.S. Pat. No. 5,352,795 discloses that, when the reaction of compound III with compound V is conducted according to the process disclosed in that patent, a competing side-reaction occurs between 4-fluorobenzonitrile V, 4-tolunitrile, an impurity of the 4-(bromomethyl)benzonitrile starting material for the preparation of letrozole, and potassium t-butoxide, leading to the formation of significant amounts the "tris" impurity VII

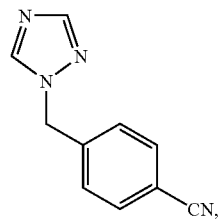

III and to a process of forming letrozole,

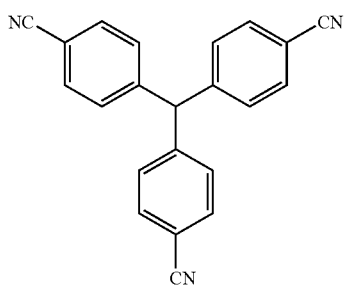

VII

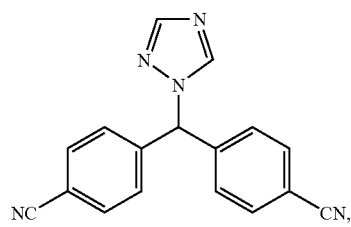

that contaminates letrozole. Moreover, the side-reaction consumes a portion of the 4-fluorobenzonitrile V reactant, requiring an excess of that reactant to complete the desired condensation of the reactant with the intermediate III.

U.S. Pat. No. 5,280,035 describes a process for preparing compound III by the reaction of 1,2,4-triazole with sodium hydride in dimethylformamide, followed by addition of 4-(bromomethyl)benzonitrile at 5° C. To obtain the desired purity, compound III must be isolated by column chromatography.

U.S. Patent Application Publication No. 2005/0209294 also describes a process for preparing compound III by reaction of 1,2,4-triazole sodium salt with 4-(bromomethyl)benzonitrile in dimethylformamide. Compound II is isolated by crystallization with greater than 96% selectivity, and, thus, contains a high percentage of compound IV. In example I of U.S. Patent Application Publication No. 2005/0209294, the extraction was done without distilling away the dimethylformamide, and adding dichloromethane and water. The organic phase gives a less efficient separation of the 2 isomers, such that, after precipitation, the ratio is 96/4.

Therefore, a need exists for a process that minimizes or substantially eliminates the formation of the impurities, compound IV and compound VII, in the synthesis of the intermediate III, and of letrozole, respectively.

SUMMARY OF THE INVENTION

The invention provides a process for preparing 4-[1-(1,2,4-triazolyl)methyl]benzonitrile, intermediate III, of formula through the preparation of intermediate III. The process of the invention for preparing intermediate III comprises combining a 4-(halomethyl)benzonitrile with a salt of 1H-1,2,4-triazole and a solvent selected from a group consisting of dimethylacetamide, N-methyl-2-pyrrolidone, and a mixture thereof, thereby forming intermediate III.

In accordance with the invention, letrozole may be prepared in a process, comprising combining 4-[1-(1,2,4-triazolyl)methyl]benzonitrile (intermediate III) with 4-halobenzonitrile, an organic solvent selected from the group consisting of dimethylformamide, dimethylacetamide, tetrahydrofuran, N-methyl-2-pyrrolidone, and mixtures thereof, and a base selected from sodium bis(trimethylsilyl)amide, hexyl lithium, butyl lithium, lithium diisopropylamide, alkoxide and mixtures thereof.

In accordance with the invention, letrozole may also be prepared in a process, comprising reacting a 4-(halomethyl)benzonitrile with a salt of 1H-1,2,4-triazole to form 4-[1-(1,2,4-triazolyl)methyl]benzonitrile, intermediate III, isolating the resulting intermediate III, combining the isolated intermediate III with a 4-halobenzonitrile, and adding a base selected from the group consisting of sodium bis(trimethylsilyl)amide, hexyl lithium, butyl lithium, lithium diisopropylamide, alkoxides, and mixtures thereof, forming letrozole.

In accordance with the invention, letrozole may also be prepared in a one-pot process, comprising reacting a 4-(halomethyl)benzonitrile with a salt of 1H-1,2,4-triazole to form 4-[1-(1,2,4-triazolyl)methyl]benzonitrile, intermediate III, combining the resulting intermediate III with a 4-halobenzonitrile, and adding a base selected from the group consisting of sodium bis(trimethylsilyl)amide, hexyl lithium, butyl lithium, lithium diisopropylamide, alkoxides, and mixtures thereof, forming letrozole, wherein the intermediate III is not isolated prior to its reaction with the 4-halobenzonitrile.

The invention also provides a process for decolorizing letrozole, comprising treating letrozole with activated charcoal in the presence of a reducing agent

DETAILED DESCRIPTION OF THE INVENTION

The present invention provides a process for preparing letrozole through the intermediate 4-[1-(1,2,4-triazolyl)methyl]benzonitrile III

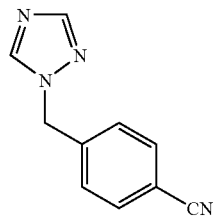

III which minimizes formation of impurities such as the isomer 4-[1-(1,3,4-triazolyl)methyl]benzonitrile IV

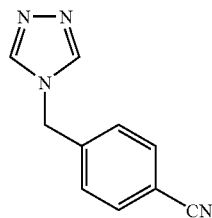

IV

The process of the invention is suitable for industrial scale, as it may be used to produce a product of sufficient purity that can be purified by industrial scale purification processes, such as crystallization or extraction, rather than column chromatography. Since a highly pure form, typically greater than 99.5 percent, of any drug is generally required for human treatment, a method that combines the control of the formation of isomers and a facile final purification is particularly advantageous. By industrial scale it is meant a process that produces a batch of at least 500 grams, more preferably a batch of at least about 1 Kg.

In one embodiment, the present invention provides a process for the preparation of 4-[1-(1,2,4-triazolyl)methyl]benzonitrile (intermediate III)

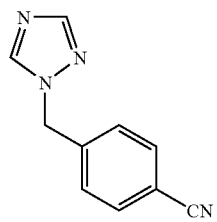

III by combining a 4-(halomethyl)benzonitrile with a salt of 1H-1,2,4-triazole and a solvent selected from the group consisting of dimethylacetamide, N-methyl-2-pyrrolidone, or a mixture thereof.

The salt of 1H-1,2,4-triazole may be a metal salt such as an alkali metal or alkaline metal salt, preferably 1,2,4-triazolyllithium, 1,2,4-triazolylsodium, or 1,2,4-triazolylpotassium, more preferably, 1,2,4-triazolylsodium or 1,2,4-triazolylpotassium.

Useful 4-(halomethyl)benzonitriles include 4-(bromomethyl)benzonitrile, 4-(chloromethyl)benzonitrile, or 4-iodomethyl benzonitrile, where 4-(bromomethyl)benzonitrile is most preferred.

The 4-(halomethyl)benzonitrile and 1H-1,2,4-triazole salt are preferably used in a mole ratio of halonitrile:triazole salt of from about 1:1 to about 1:2, preferably from about 1:1 to about 1:1.1.

The solvents are preferably used in an amount of from about 10 to about 50 parts by weight of solvent based on the amount of 4-(bromomethyl)benzonitrile. When the reaction is performed in dimethylacetamide, the amount of isomer IV impurity obtained is half the amount obtained when the reaction is performed in dimethylformamide. The preferred solvent is dimethylacetamide.

The starting material may be combined in different manners. In a preferred embodiment, the 4-(halomethyl)benzonitrile is added portion-wise to the mixture of dimethylacetamide and 1H-1,2,4-triazole salt. The process is preferably carried out at a temperature of less than about 30° C., more preferably less than about 5° C., and, most preferably, less than about 0° C. A particularly preferred temperature range is from about −20° C. to about 0° C.

As stated above, this process allows for obtaining intermediate III with such purity that a purification process suitable for industrial scale may be used to further purify Intermediate III. For example, the obtained intermediate III may be further purified by extraction process involving an aqueous phase and a water immiscible phase.

The water immiscible phase preferably contains a $C_5$ to $C_{12}$, more preferably, $C_6$ to $C_{10}$, linear, branched or cyclic saturated and aromatic hydrocarbon, such as toluene, benzene, and hexane. Preferably the water immiscible phase contains toluene. The water immiscible solvent for extraction of intermediate III should have a selective solubility regarding the isomeric impurity IV, which is slightly more polar than intermediate III, and, more preferably, more soluble in water than in the immiscible solvent. Therefore, the solvent must not be a very strong solvent for these compounds. Toluene, preferably warmed and associated with the salting of water, is the preferred solvent for this extraction, as, after precipitation, the ratio is 98.5/1.5.

A repetition of the process disclosed in U.S. Patent Application Publication No. 2005/0209294 indicated that the crystallization was quite ineffective in removal of the isomer, and that the reduction in isomer is achieved only during the extraction phase (from ca. 10% to ca. 5%). Due to the low selectivity of the disclosed extraction (dimethylformamide/dichloromethane), a significant amount of product is left in the aqueous phase, such that, if the extraction were to be repeatedly and exhaustively, the extract and subsequent crystalline intermediate would contain approximately 10% of isomer, as does the reaction mixture. In contrast, in the process of the present invention, toluene selectively dissolves the product, substantially leaving the impurity in the aqueous phase. US 2005/0209294 also fails to disclose any conversion of the intermediate containing 4-5% of isomer into letrozole of USP quality (i.e. <0.3% of impurity A). It appears that if conventional prior art procedures are followed, all of which are designed to use pure intermediate, the isomer reduction would be insufficient to meet the USP specification.

To manipulate the solubility of the various impurities/intermediate II, it is possible to add an ionic agent to the aqueous phase. In one embodiment, the aqueous phase contains an aqueous solution of sodium chloride Preferably, the intermediate III is extracted at least twice, using from about 15 to about 20 ml of water immiscible solvent, such as toluene, per gram of intermediate III and from about 4 to about 6 ml of an about 20 to about 27 percent by weight water (or solution of sodium chloride) per gram of intermediate III.

The extraction process is preferably carried out at a temperature of about 20° to about 50° C., preferably, from about 40° to about 45° C.

Two toluene extractions, followed by precipitation with isooctane, isolate the bulk of the intermediate III with a purity of greater than about 98.5 percent by weight. In addition, due to its volatility, 4-tolunitrile, if present, is substantially removed together with the toluene during concentration. The purification procedure can thus provide a yield of greater than about 80 percent by weight, preferably greater than about 82 percent, more preferably, from about 82 to about 90 percent, and, most preferably, from about 83 to about 84 percent by weight, having an isomer IV impurity content of less than about 1.5 percent by weight, based on the amount of starting material I.

The process of the present invention results in intermediate III with less than about 9 percent by weight of the isomer IV in the crude reaction mixture, preferably, with less than about 5 percent by weight of the isomer IV in the crude reaction mixture. Preferably, intermediate III is obtained after extraction and precipitation in a yield of about 83 to about 84 percent by weight, having an isomer IV content of less than about 1.5% by weight, based on the amount of starting material I.

The intermediate III can, if desired, be isolated in crystalline form, e.g., by crystallization from a $C_5$ to $C_{12}$, preferably, $C_6$ to $C_{10}$, aromatic or saturated hydrocarbon. Examples of suitable solvents include a mixture of toluene and isooctane, hexane, heptane, and isomeric mixtures thereof. Any residual 4-tolunitrile remains in the mother liquor.

The intermediate III may be further purified as its acid salt, e.g., the hydrochloride, hydrobromide, or methanesulfonate, further reducing the content of the isomer IV, preferably to less than about 0.1 percent by weight. This purification is not necessary commercially, however, as an intermediate III containing a higher level of the isomer IV can be used satisfactorily in the synthesis of letrozole, forming letrozole that meets the U.S.P. requirements, including those requirements for the content of letrozole related compound A.

The intermediate III prepared by the process of the present invention may then be converted to letrozole. The conversion may be carried out by prior art processes, such as that disclosed in U.S. Pat. No. 4,978,672.

In accordance with the invention, intermediate III is combined with a 4-halobenzonitrile, an organic solvent, and a base selected from the group consisting of sodium bis(trimethylsilyl)amide, hexyl lithium, butyl lithium, lithium diisopropylamide, alkoxides, and mixtures thereof, is added, forming letrozole. Preferably, the 4-(halomethyl)benzonitrile is reacted with the salt of 1H-1,2,4-triazole in dimethylacetamide. Preferably, the base is sodium bis(trimethylsilyl) amide. In another embodiment, the base is an alkali metal alkoxide, such as potassium t-butoxide, particularly used in combination with DMF.

In accordance with the invention, the base is preferably added at a rate that avoids high concentrations of base. More preferably, the base is added at a rate of about from about 0.077 to about 0.0077 moles per minute per mole of intermediate III. Most preferably, the base is added dropwise. Adding the base at a rate that avoids high concentrations of base, where the base is the preferred base, results in a less colored letrozole than provided by the prior art.

In a preferred embodiment, intermediate III is reacted with 4 halobenzonitrile and a base, such as sodium bis(trimethylsilyl)amide, hexyl lithium, butyl lithium, lithium diisopropylamide, and mixtures thereof, where sodium bis(trimethylsilyl)amide. This process can be carried out in one pot with one of the two solvents used to prepare intermediate III.

In one embodiment, 4-halobenzonitrile is 4-fluorobenzonitrile.

In one embodiment, the 4-halobenzonitrile and intermediate III are mixed in a mole ratio of from about 0.9:1 to about 1.1:1, preferably, from about 0.95:1 to about 1.05:1. The base and intermediate III are used in a mole ratio of from about 2:1 to about 3:1, preferably, from about 2.1:1 to about 2.5:1. Preferably, the intermediate III and the 4-halobenzonitrile react in a polar aprotic organic solvent, such as dimethylformamide, dimethylacetamide, tetrahydrofuran, N-methyl-2-pyrrolidone, or a mixture thereof, where from about 10 to about 50 ml of solvent are present per gram of intermediate III. Preferably the solvents are dimethylacetamide and N-methyl-2-pyrrolidone.

To reduce or eliminate the reaction between the base and the 4-halobenzonitrile, the base is added at a rate that avoids high concentrations of base, such as by adding the base dropwise. Preferably, the base is added at a rate of from about 0.077 to about 0.0077 moles per minute per mole of intermediate III. The preferred solvents for use with the base are dimethylacetamide and N-methyl-2-pyrrolidone.

In a preferred embodiment, letrozole is prepared by a one-pot process comprising preparing intermediate III, as described above, and reacting intermediate III directly with the 4-halobenzonitrile and a base, which is added dropwise, in a one-pot process without isolating the intermediate III. The 4-halobenzonitrile and intermediate III are mixed in a mole ratio of from about 0.9:1 to about 1.1:1, preferably, from about 0.95:1 to about 1.05:1, and a suitable base, and the intermediate III is not isolated prior to its reaction with the 4-halobenzonitrile. The base and intermediate III are used in a mole ratio of from about 3:1 to about 2:1 preferably from about 2.1:1 to about 2.5:1.

Preferably, the base is selected from the group consisting of sodium bis(trimethylsilyl)amide, hexyl lithium, butyl lithium, lithium diisopropylamide, alkoxide, and mixtures thereof, and, more preferably, the base is sodium bis(trimethylsilyl)amide. When the base is an alkoxide, preferably, t-butoxide, the solvent is dimethylformamide. When the base is the preferred base sodium bis(trimethylsilyl)amide, the solvent is dimethylacetamide. The base is preferably added at a rate that avoids high concentrations of base, such as by adding the base dropwise, preferably, at a rate of from about 0.077 to about 0.0077 equivalents of base per minute per gram of letrozole. Preferably, the reaction is performed in a solvent selected from the group consisting of dimethylacetamide, dimethylformamide, or tetrahydrofuran.

Most preferably, the base is sodium bis(trimethylsilyl)amide, which may be prepared from hexamethyldisilazane and sodium amide, or purchased as a 40 percent solution in tetrahydrofuran. To avoid reaction between the 4-fluorobenzonitrile V and the sodium bis(trimethylsilyl)amide, the base is preferably added gradually to the mixture of synthons (all known procedures first generate the anion of intermediate III prior to bringing it into contact with 4-fluorobenzonitrile V).

Approximately equimolar amounts of the intermediate III and 4-fluorobenzonitrile V in dimethylacetamide, dimethylformamide, or tetrahydrofuran provide a yield of about 85 percent by weight of pure letrozole after isolation and purification. As no stoichiometric excess of 4-fluorobenzonitrile V is required, any side-reactions with the base are believed to be negligible.

Where the base is one of sodium bis(trimethylsilyl)amide, hexyl lithium, butyl lithium, lithium diisopropylamide, and mixtures thereof, and is added dropwise in the one-pot process, the resulting letrozole is a less colored letrozole, and is significantly less colored than the yellow letrozole prepared with prior art methods. Using lithium diisopropylamide, letrozole having a purity of about 99.7 percent by weight may be obtained in a yield of 75 percent by weight. The product of that synthesis is less colored than the product made using potassium t-butoxide. Where the product is colored, it is typically a slightly yellowish color.

The letrozole produced using sodium bis(trimethylsilyl) amide as the base is already substantially less colored after isolation of the crude than letrozole prepared with prior art processes. One or more of the following additional optional steps may be taken to further purify the letrozole: the crude product may be further purified by crystallization from, e.g., aqueous acetone or aqueous dimethylformamide or aqueous dimethylacetamide may be used to lower the content of letrozole related compound A,

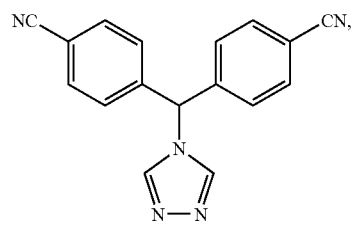

VI compound VI; and, during recrystallization, a charcoal discoloration may be effected, preferably, in the presence of sodium metabisulfite, to avoid degradation of the letrozole.

Decoloration of the product using activated charcoal may cause extensive degradation, resulting in the formation of significant amounts of benzoquinone Cp 9425:

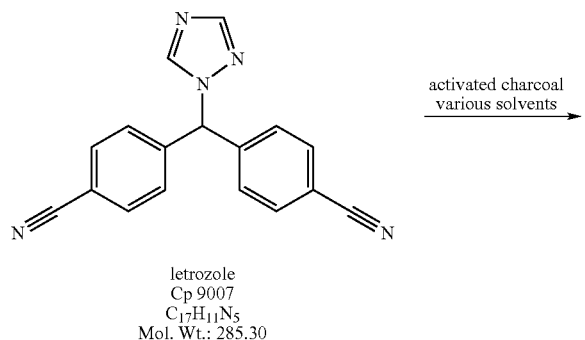

letrozole
Cp 9007
$C_{17}H_{11}N_5$
Mol. Wt.: 285.30

-continued

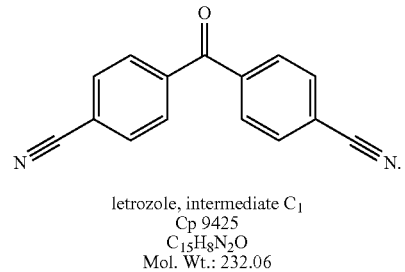

letrozole, intermediate $C_1$
Cp 9425
$C_{15}H_8N_2O$
Mol. Wt.: 232.06

The present invention also provides a process for decolorizing letrozole with activated charcoal in the presence of a reducing agent. This process avoids extensive degradation to the product.

Preferably, the reducing agent is sodium metabisulfite. However, other reducing agents that are useful in neutral or slightly acidic media, such as thiosulphate, may be used.

In one embodiment, the letrozole is preferably first mixed with a water-miscible solvent, such as acetone, DMA, and NMP, preferably, in an amount of from about 12 to about 18 ml per gram of letrozole, and water, preferably, from about 1 to about 1.5 ml per gram of letrozole. The mixture is then stirred, preferably at ambient temperature, until dissolved. An aqueous solution of the reducing agent, preferably, from about 0.04 to about 0.2 grams per gram of letrozole, more preferably, from about 0.045 to about 0.055 grams per gram of letrozole, followed by from about 0.04 to about 0.2 grams of activated charcoal per gram of letrozole, preferably, from about 0.045 to about 0.055 grams per gram, is combined with the solution. The resulting suspension is stirred at ambient temperature for preferably from about 0.2 to about 1.0 hours, and the charcoal is filtered off and rinsed with a mixture of acetone, preferably, from about 1 to about 4 grams per gram of letrozole, and water, preferably, from about 0.1 to about 0.5 grams per gram of letrozole. The clear filtrates are heated to from about 45° to about 55° C., and diluted with water, preferably, from about 15 to about 30 grams per gram of letrozole.

The mixture is then heated until a solution is obtained, and allowed to cool to ambient temperature under slow agitation. The resulting precipitate is collected, rinsed well with water at from about 10° to about 50° C., and dried.

In one embodiment, the color is reduced or eliminated without degradation by dissolving the letrozole in 90 percent aqueous acetone, containing a reducing agent, such as sodium metabisulphite, followed by treatment of the resulting solution at room temperature with 10 percent activated charcoal, clarification, and precipitation by dilution with water.

Letrozole prepared with any process in accordance with the invention may also be purified by crystallization, preferably from a mixture of water and a water-miscible solvent, such as dimethylformamide, acetone, methylpyrrolidone, and/or dimethylacetamide. In a preferred process of the invention, letrozole crystals are dissolved in a mixture of from about 10 grams to about 15 grams of acetone and from about 1 gram to about 1.5 grams of water per gram of letrozole, filtered, and diluted at the boiling point with from about 15 to about 30 grams of water per gram of letrozole. The resulting suspension is stirred for from about 2 to about 20 hours at ambient temperature, and the suspension is collected, rinsed with water, and dried under vacuum at from about 30° to about 90° C.

The salt of 1H-1,2,4-triazole used in the processes of the present invention as a starting material may be prepared by different processes. It may be prepared by mixing 1H-1,2,4-triazole with a metal hydroxide, such as potassium hydroxide or sodium hydroxide, in a mole ratio of from about 1.1:1 to about 0.9:1 preferably, from about 1.05:1 to about 0.95:1 and, more preferably, from about 1.01:1 to about 0.99:1 in a polar organic solvent such as methanol, and heating the mixture to at least about 20° to about 70° C., preferably from about 40° to about 64° C., more preferably to about 60° C., until a solution is formed. The solution is preferably then concentrated under vacuum to a semi-crystalline residue of the 1H-1, 2,4-triazole salt. Preferably, dimethylformamide is then added, and the mixture is further concentrated to remove the polar organic solvent and water. The resulting salt may then be used to prepare the intermediate III, as described above.

EXAMPLES

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Example 1

Preparation of Intermediate III

A glass reactor was charged with 55 grams of 1H-1,2,4-triazole, 52.6 grams of potassium hydroxide, and 250 grams of methanol, and heated to 60° C. until a solution formed. The solution was concentrated under vacuum to a semi-crystalline residue of 1,2,4-triazolylpotassium. Then, 250 grams of dimethylformamide were added, and the mixture was further concentrated to remove methanol and water. The mixture was then diluted with 1125 grams of dimethylformamide, and the mixture was cooled to a temperature of −10° C. While maintaining the temperature of the mixture below 5° C., 125 grams of 4-(bromomethyl)benzonitrile were added in portions. After a period of 30 minutes, the reaction mixture, comprising intermediate III and isomer IV impurity in a ratio of 90:9, was concentrated under vacuum to a weight of 325 grams, and then diluted with 625 grams of water, containing 188 grams of sodium chloride. After the addition of the sodium chloride solution, 1250 grams of toluene were added, the mixture was stirred for 30 minutes at 40° C., and then allowed to stratify. The toluene phase was separated, and the aqueous phase re-extracted in the same manner with a further 375 grams of toluene. The combined toluene extracts were dried with 60 grams of anhydrous sodium sulfate, concentrated to 325 grams, and diluted with 500 grams of isooctane. The suspension was stirred at ambient temperature for 1 hour, and the precipitate of the intermediate III was collected and rinsed with isooctane. After drying at 60° C. for 16 hours, 98 grams of the intermediate III, having a purity of 98.6 percent by weight and an isomer IV impurity content of 1.3 percent by weight, were obtained.

Example 2

Preparation of Intermediate III

A glass reactor was charged with 46.2 grams of 1H-1,2,4-triazole, 44.2 grams of potassium hydroxide, and 250 grams of methanol, and heated to 60° C., until a solution was obtained. The solution was concentrated under vacuum to a semi-crystalline residue of 1,2,4-triazolylpotassium. Then, 250 grams of dimethylformamide were added, and the mixture further concentrated to remove the methanol and water. The mixture was diluted with 1125 grams of dimethylformamide, and the temperature was adjusted to −10° C. While maintaining the temperature below 5° C., 125 grams of 4-(bromomethyl)benzonitrile were added in portions. After a further 30 minutes, the reaction mixture, containing a ratio of intermediate III to unwanted isomer IV of 90.6:9.4, was concentrated under vacuum to a weight of 300 grams, and diluted with 625 grams of water containing 188 grams of sodium chloride. Then, 1250 grams of toluene were added, the mixture was stirred for 30 minutes at 45° C., and then allowed to stratify. The toluene phase was separated, and the aqueous phase re-extracted in the same manner using a further 375 grams of toluene. The combined toluene extracts were dried with 63 grams of anhydrous sodium sulfate, and concentrated to an oily residue of intermediate III, having an unwanted isomer IV content of 1.3 percent by weight.

Example 3

Preparation of Intermediate III

A glass reactor was charged with 1 gram of 4-(bromomethyl)benzonitrile and 50 grams of dimethylacetamide, and the temperature was adjusted to 0° C. Then, 0.57 grams of 1,2,4-triazolylsodium were added, the mixture was stirred at 0° C. for 60 minutes, and then analyzed using HPLC. The reaction mixture contained intermediate III and unwanted isomer in a ratio of 96:4, and no residual 4-(bromomethyl)benzonitrile was detected.

Example 4

Selectivity in the Preparation of Intermediate III

The procedure of Example 3 was repeated with various solvents and bases, and the reaction mixtures were analyzed using HPLC to determine the ratio of intermediate III to isomer IV impurity. Solvents used were acetonitrile (ACN), chloroform ($CHCl_3$), dimethylformamide (DMF), dichloromethane ($CH_2Cl_2$), acetone, $CH(OC_2H_5)_2$, N-methyl-2-pyrrolidone (MP), dimethylacetamide (DMA), methanol, water, toluene, and mixtures thereof. Bases used were sodium iodide (NaI), potassium t-butoxide (KOtB), potassium hydroxide (KOH), potassium carbonate (K2CO3), potassium iodide (KI), commercial sodium triazolate (NAT), tetrabutyl ammonium hydroxide (TBAI), and mixtures thereof. The results are summarized in Table 1 below, in which the units of dilution are parts by weight of solvent based on the weight of the 4-(bromomethyl)benzonitrile.

TABLE 1

| Run | Solvent | Base | Dilution | Temp. | Time (hrs) | Isomer ratio | Yield | Note |
|---|---|---|---|---|---|---|---|---|
| 1 | ACN/CHCl$_3$ |  | 15 | 50° C. | 0.5 | 1.5 | 26.1% |  |
| 2 | DMF | NaI | 18 | 22° C. | 240 | 0.6 |  |  |
| 3 | CH$_2$Cl$_2$ | NaI | 20 | 22° C. | 0.5 |  | 0% |  |
| 4 | DMF | KOtB | 14 | 22° C. | 0.2 | 7.5 | 61% | suspension |
| 5 | DMF | KOH | 13 | 5° C. | 0.5 | 10 | 42% |  |
| 6 | DMF | KOH | 13 | 5° C. | 1 | 11 | 23% | incomplete |
| 7 | DMF | KOH | 45 | 5° C. | 15 | 11.6 |  |  |
| 8 | Acetone | K$_2$CO$_3$/NaI | 25 | 55° C. | 15 | 4.5 |  |  |
| 9 | Acetone | K$_2$CO$_3$/KI | 25 | 55° C. | 8 | 4.9 |  |  |
| 10 | DMF | NAT | 15 | 5° C. | 0.5 | 12.4 |  |  |
| 11 | DMF | KOH | 15 | 5° C. | 0.5 | 12.4 |  |  |
| 12 | MP | NAT | 15 | 5° C. | 0.5 | 15.3 | 70% |  |
| 13 | CH(OC$_2$H$_5$)$_2$ | NAT | 30 | 22° C. | 24 | 3 | 3% reaction |  |
| 14 | MP | NAT | 11.5 | 5° C. | 1 | 12.7 |  | suspension |
| 15 | MP | NAT-H$_2$O | 11.5 | 5° C. | 1 | 11.8 |  |  |
| 16 | MP | KOH | 35 | 5° C. | 1 | 10.5 |  |  |
| 17 | MP | NAT | 35 | −20° C. | 0.5 | 15 |  | 20% SM |
| 18 | MP | NAT | 15 | −30° C. | 1 | 16− |  |  |
| 19 | MP | NAT | 35 | 10° C. | 0.5 | 13.8 |  | 6.9% SM gelification |
| 20 | MP/DMA | NAT | 23 | −33° C. | 2 | 15.4 |  |  |
| 21 | MP | NAT | 14 | −22° C. | 2 | 15.1 | 57% | fluid gel |
| 22 | DMA | NAT | 50 | 20° C. | 0.5 | 21 |  | Purified as hydrochloride |
| 23 | MP | NAT | 50 | 20° C. | 0.5 | 13.3 |  |  |
| 24 | DMF | NAT | 50 | 20° C. | 0.5 | 11.5 |  |  |
| 25 | Methanol | NAT | 50 | 20° C. | 0.5 | 5.7 |  |  |
| 26 | DMSO | NAT | 50 | 20° C. | 0.5 | 4.6 |  |  |
| 27 | CH$_2$Cl$_2$/H$_2$O | NAT/TBAI | 50 | 20° C. | 0.5 | 5.7 |  |  |
| 28 | Toluene/H$_2$O | NAT/TBAI | 50 | 20° C. | 0.5 | 4.6 |  | 2 phases |
| 29 | DMF | K$_2$CO$_3$/NaI | 25 | 22° C. | 20 | 8.4 |  | 2 phases |
| 30 | DMF | KOH | 10 | 0° C. | 1 | 9.2 |  | Sum of isomers only 76.7% |
| 31 | DMA | NAT | 50 | 24° C. | 0.5 | 19.5 |  | Sum of isomers 89.7% |
| 32 | DMA | (1.05M) NAT | 10 | −5° C. | 1.5 | 16.2 | 67% |  |
| 33 | DMA | (2.15M) NAT | 50 | 0° C. | 1 | 21.6 |  |  |
| 34 | DMA | (1.08M) NAT | 20 | 0° C. | 1.5 | 17 |  | Cp 20517 present |
| 35 | DMA | (1.07M) NAT | 13 + 2 | 4° C. | 1.5 | 14.3 |  |  |
| 36 | DMA | (1.07M) NAT | 13 + 2 | −16° C. | 2 | 17.2 |  |  |

As illustrated in Table 1, choice of solvent has the largest effect on the resulting ratio of intermediate III to isomer IV impurity. Choice of base, dilution, and reaction times/temperatures also affect the ratio of intermediate III to isomer IV impurity, but to a lesser degree. Dimethylacetamide solvent showed the most selectivity for intermediate III, followed by methylpyrrolidone.

Example 5

Preparation of Letrozole from Intermediate III Using the New Base

To the oily residue of intermediate III, from example 2, 63 grams of 4-fluorobenzonitrile and 2064 grams of tetrahydrofuran were added. At 0 to 5° C. under a nitrogen atmosphere, 480 grams of a 40 percent sodium bis(trimethylsilyl)amide in THF solution were add dropwise over a period of 2 hours. After the addition was complete, the reaction mixture was quenched by the addition of 206 grams of acetic acid, followed by 1030 grams of water. After 15 minutes under agitation, the two-phase reaction mixture was allowed to stratify, and the organic phase was separated, and concentrated under vacuum to a volume of about 500 ml. The solution was then twice diluted with 500 grams of toluene, and again concentrated to about 500 ml. The resulting suspension was cooled to 10° C. for 90 minutes, and the precipitate of letrozole was collected, rinsed with toluene, and dried, providing 128 grams of product. Half of the crystals, i.e., 64 grams, were dissolved in a mixture of 640 grams of acetone and 77 grams of water. A solution of 2.56 grams of sodium metabisulfite in 77 grams of water was then added, followed by 6.4 grams of activated charcoal. The resulting suspension was stirred at ambient temperature for 1 hour, and the charcoal was filtered off and rinsed with a mixture of 150 grams of acetone and 20 grams of water. The clear filtrates were concentrated under vacuum (ca. 200 grams of distillate), heated to about 60° C., and diluted with 1050 grams of water. The mixture was allowed to cool to ambient temperature under slow agitation. The resulting precipitate was collected, rinsed with water, and dried under vacuum at 80° C., yielding 59 grams of product, having an HPLC purity of 99.87 HPLC area percent, and a letrozole related compound A content of 0.13 HPLC area percent.

Example 6

Preparation of Letrozole from Intermediate III Using the New Base

A glass reactor was charged with 30 grams of intermediate II, having an isomer IV impurity content of 0.1 percent by weight, 19.7 grams of 4-fluorobenzonitrile, and 800 grams of tetrahydrofuran. Then, 160 grams of a 40 percent solution of sodium bis(trimethylsilyl)amide in THF was add dropwise at 0° to 2° C. under a nitrogen atmosphere. After the addition was complete, the reaction mixture was quenched by the addition of 60 grams of acetic acid, followed by 300 grams of water. After 30 minutes under agitation, the reaction mixture was allowed to stratify, and the organic phase was concentrated under vacuum to a volume of about 150 ml, diluted with 150 grams of toluene, and again concentrated to about 150 ml. The suspension was cooled to ambient temperature, and the precipitate of letrozole was collected, rinsed with toluene, and dried, yielding 41 grams of product. The crystals were dissolved in a mixture of 400 grams of acetone and 40 grams of water, filtered, and diluted at the boiling point with 750 grams of water. The suspension was stirred overnight at ambient temperature, and the suspension was collected, rinsed with water, and dried under vacuum at 80° C., yielding 37 grams of product.

Example 7

Preparation of Letrozole from Intermediate III Using the New Base

A glass reactor was charged with 30 grams of intermediate III, 19.7 grams of 4-fluorobenzonitrile, and 300 grams of dimethylacetamide. Then, a 40 percent by weight solution of 150 grams of sodium bis(trimethylsilyl)amide solution in THF was added at –10° C. to –5° C. under a nitrogen atmosphere over a period of 50 minutes. After the addition was complete, the reaction mixture was stirred at ca. 0° C. for 60 minutes, then quenched by the addition of 60 grams of acetic acid dissolved in 180 grams of water, followed by 1200 grams of water. The suspension was stirred overnight at ambient temperature, then cooled to about 5° C. and the precipitate was collected, rinsed with water, and dried under vacuum at 60° C., providing a yield of 43 grams, having a purity of 99.4 HPLC area percent.

Example 8

Preparation of Letrozole by a Drop-Wise Addition of Potassium Tert-Butoxide

A glass reactor was charged with 10 grams of intermediate III, 7.2 grams of 4-fluorobenzonitrile, and 200 grams of dimethylformamide. Then, a solution of 13.4 grams of potassium tert-butoxide in 100 grams of dimethylformamide was added at –20° C. to –15° C. under a nitrogen atmosphere over a period of 50 minutes. After the addition was complete, the reaction mixture was quenched by the addition of 20 grams of acetic acid, followed by 50 grams of water, and evaporated under vacuum to a semi-crystalline residue. The reaction residue was triturated at 40° C. with 200 grams of water, and, after 15 minutes without cooling, the suspension was collected, rinsed with water, and dried under vacuum at 60° C., providing a yield of 14.4 grams, having a purity of 99.5 HPLC area percent.

Example 9

One-Pot Preparation of Letrozole

A glass reactor was charged with 24.3 grams of 1,2,4-triazolylsodium and 500 grams of dimethylformamide. At a temperature between –10° C. and 0° C., 50 grams of 4-(bromomethyl)benzonitrile (53.2 grams with a purity of about 94 percent by weight, containing about 6 percent by weight of 4-tolunitrile) were added in portions. After stirring at 0° C. for 1 hour, 30.9 grams of 4-fluorobenzonitrile were added, and, while maintaining a temperature of –5° C. to –10° C., 245 grams of a 40 percent solution of sodium bis(trimethylsilyl)amide in THF were added dropwise. After the addition was completed, the reaction was quenched by the addition of 200 grams of 50 percent acetic acid, followed by precipitation of the product by the addition of 1500 grams of water. The resulting suspension was stirred and cooled to about 15° C., and the precipitate was collected and rinsed with water. The wet precipitate was dissolved in 350 grams of dichloromethane, and the solution washed with 250 grams of water. The organic phase was separated, concentrated to a volume of about 200 ml, diluted with 250 grams of toluene, and concentrated to a volume of about 300 ml. The resulting suspension was stirred at ambient temperature for 1 hour, and the precipitate was collected, rinsed with toluene, and dried, yielding 52 grams of crude letrozole product.

Example 10

One-Pot Preparation of Letrozole

A glass reactor was charged with 46 grams of 1,2,4-triazolylsodium and 1350 grams of dimethylacetamide. At a temperature between –15° C. and –10° C., 90 grams of 4-(bromomethyl)benzonitrile (95 grams of industrial grade having a purity of about 94 percent by weight, containing about 6 percent by weight of 4-tolunitrile) were added over a period of 30 minutes. After stirring at a temperature between –15° C. and –10° C. for 1 hour, and then at a temperature between –5° C. and 0° C. for 1 hour, an HPLC analysis indicated a ratio of intermediate III to isomer IV of 18:1. Then, 52.8 grams of 4-fluorobenzonitrile were added, and, while maintaining a temperature of –8° C. to 0° C., 480 grams of a 40 percent solution of sodium bis(trimethylsilyl)amide in THF were added dropwise. After the addition was completed, the reaction was stirred at a temperature between –2° C. and –2° C. for 1 hour, and then the reaction was quenched by the addition of a mixture of 180 grams of acetic acid and 540 grams of water, followed by precipitation of the product by the addition of 3510 grams of water. The resulting suspension was stirred overnight at ambient temperature, i.e., from 15° C. to 25° C., and then the precipitate was collected and rinsed with water. The wet precipitate was dissolved in 630 grams of dichloromethane and 63 grams of acetone, and the solution washed with 450 grams of water. The organic phase was separated at 30° C., diluted with 450 grams of toluene, concentrated at atmospheric pressure until all the dichloromethane was removed, and then further concentrated under vacuum to a weight of about 300 grams. The suspension was diluted with a further 450 grams of toluene and again concentrated under vacuum to a weight of 500 grams. The resulting suspension was stirred at a temperature between 10° C. and 15° C. for 1 hour, and the precipitate was collected, rinsed with toluene, and dried, yielding 99 grams of letrozole with a purity of 99.3 HPLC area percent. The only detectable impurity was 0.7 HPLC area percent of letrozole related compound A. The final purification of the letrozole product is described in Example 6.

Example 11

Purification of Letrozole Using Activated Charcoal

A glass reactor was charged with 99 grams of crude letrozole from Example 3, having a letrozole related compound A of 0.7 HPLC area percent, 1000 grams of acetone, and 125 grams of water. The mixture was stirred at ambient temperature until dissolved, then a solution of 4 grams of sodium metabisulfite in 125 grams of water was added, followed by 5 grams of activated charcoal. The suspension was stirred at ambient temperature for 1 hour, and the charcoal was filtered off, and rinsed with a mixture of 200 grams of acetone and 50 grams of water. The clear filtrates were heated to about 55° C., and diluted with 1950 grams of water. The resulting suspension was heated until a solution was again obtained, and then allowed to cool overnight at ambient temperature under slow agitation. The resulting precipitate was collected, rinsed well with water at 50° C., and dried, yielding 89 grams of letrozole, having an HPLC purity of 99.95 percent by weight and a letrozole related compound A content of 0.05 percent by weight. No other impurities were detected.

Example 12

Purification of Letrozole Using Activated Charcoal

A glass reactor was charged with 52 grams of crude letrozole from Example 4, 520 grams of acetone, and 65 grams of water. The mixture was stirred at ambient temperature until dissolved, and a solution of 2 grams of sodium metabisulfite in 65 grams of water was added, followed by 7.6 grams of activated charcoal. The suspension was stirred at ambient temperature for 1 hour, and the charcoal filtered off and rinsed with a mixture of 150 grams of acetone and 38 grams of water. The clear filtrates were heated to about 55° C., and diluted with 1000 grams of water. The mixture was heated until a solution was obtained, then allowed to cool to ambient temperature under slow agitation. The resulting precipitate was collected, rinsed well with water at 50° C., and dried, yielding 41 grams of letrozole, having an HPLC purity of 99.82 percent by weight and a letrozole related compound A content of 0.18 percent by weight.

Example 13

Purification of a Salt of Intermediate III

Intermediate III was prepared using 70 grams of 4-(bromomethyl)benzonitrile with the method of Example 1. After the extraction with toluene, the solution was concentrated under vacuum to an oil, diluted with 400 grams of acetone, filtered from residual insoluble salts, and rinsed with 80 grams more of acetone. Under stirring, 37 grams of 32% concentrated aqueous hydrochloric acid was added to the solution. After 1 hour of stirring, the resulting precipitate was filtered, washed with acetone, and dried at 60° under vacuum to a constant weight of 56.3 grams of hydrochloride product, having an HPLC purity of 99.1% with 0.2% of compound III and a yield of 71.4%. Preferably, the resulting salt would be transformed to the corresponding base before use.

What is claimed is:

1. A process for preparing 4-[1-(1,2,4-triazolyl)methyl] benzonitrile having a structure of formula III,

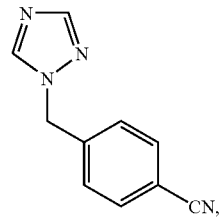

III comprising combining a 4-(halomethyl)benzonitrile with a salt of 1H-1,2,4triazole and a solvent selected from a group consisting of: dimethylacetamide, N-methyl-2-pyrrolidone, and a mixture thereof, thereby forming 4-[1-(1,2,4-triazolyl) methyl]benzonitrile; wherein said salt of 1H-1,2,4-triazole is a metal salt.

2. A process according to claim 1, wherein the 4-(halomethyl)benzonitrile is 4-(chloromethyl)benzonitrile, 4-(bromomethyl)benzonitrile or 4(iodomethyl)benzonitrile.

3. A process according to claim 2, wherein the 4-(halomethyl)benzonitrile is 4-(bromomethyl)benzonitrile.

4. A process according to any of claims 1, claim, wherein the salt of 1H-1,2,4triazole is an alkali metal or alkaline earth metal salt.

5. A process according to claim 4, wherein the salt of 1H-1,2,4-triazole is 1,2,4-triazolylsodium or 1,2,4-triazolylpotassium.

6. A process according to claim 4, wherein the solvent is dimethylacetamide.

7. A process according to claim 4, wherein the solvent is N-methyl-2-pyrrolidone.

8. A process according to any of claims 1, wherein the 4-[1-(1,2,4-triazolyl)methyl]benzonitrile is prepared at a temperature of less than about 30° C.

9. A process according to claim 8, wherein the temperature is from about −20° C. to about 0° C.

10. A process according to any of claims 1, further comprising extracting impurities from 4-[1-(1,2,4-triazolyl)methyl]benzonitrile the in a two phase system.

11. The process according to claim 10, where in the two phase system comprises an aqueous phase and a water immiscible phase, the water immiscible phase comprising a $C_5$ to $C_{12}$ linear, branched, or cyclic saturated and aromatic hydrocarbon.

12. The process according to claim 11, wherein the water immiscible phase comprises at least one hydrocarbon selected from the group consisting of toluene, benzene, and hexane.

13. The process according to claim 11, wherein the water immiscible phase comprises toluene.

14. A process according to claim 1, wherein 4-[1-(1,3,4-triazolyl)-methyl]benzonitrile having the formula IV:

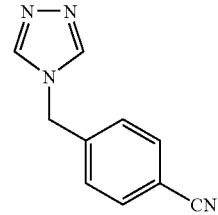

IV is obtained in an amount of less than about 10 percent by weight.

15. A process for the preparation of letrozole,

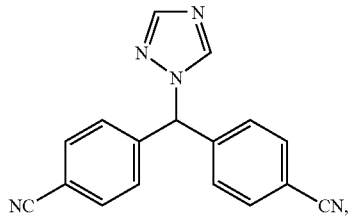

comprising combining 4-[1-(1,2,4-triazolyl)methyl]benzonitrile according to the process of claim 1, with 4-halobenzonitrile, an organic solvent selected from the group consisting of dimethylformamide, dimethylacetamide, tetrahydrofuran, N-methyl-2-pyrrolidone, and mixtures thereof, and a base selected from sodium bis(trimethylsilyl)amide, hexyl lithium, butyl lithium, lithium diisopropylamide, alkoxide and mixtures thereof.

16. A process according to claim 15, wherein the base is sodium bis(trimethylsilyl)amide.

17. A process according to claim 15, wherein the 4-halobenzonitrile is selected from 4-fluorobenzonitrile, 4-chlorobenzonitrile, and 4-bromobenzonitrile.

18. A process according to claim 17, wherein the 4-halobenzonitrile is 4-fluorobenzonitrile.

19. A process according to claim 15, wherein the reaction is conducted in the presence of a polar aprotic solvent.

20. A process according to claim 19, wherein the solvent is selected from the group consisting of dimethylformamide, dimethylacetamide, tetrahydrofuran, N-methyl-2-pyrrolidone, and mixtures thereof.

21. A process according to claim 20, wherein the solvent is selected from the group consisting of dimethylacetamide and N-methyl-2-pyrrolidone, optionally, in a mixture with THF or dimethylformamide.

22. A process according to claim 15, wherein the base is added to a mixture of 4-[1-(1,2,4-triazolyl)methyl]benzonitrile and the 4-halobenzonitrile.

23. A process according to claim 22, wherein the base is added dropwise.

24. A process according to claim 23, wherein the base is added at a rate of about 0.077 to about 0.0077 moles per minute per mole of 4-[1-(1,2,4-triazolyl)methyl]benzonitrile.

25. A process for the preparation of letrozole comprising:
(a) preparing 4-[1-(1,2,4-triazolyl)methyl]benzonitrile according to the process of any of claims 1, and
(b) converting the 4-[1-(1,2,4-triazoly)methyl]benzonitrile to letrozole.

26. The process according to claim 25, further comprising converting the 4-[1-(1,2,4-triazoly)methyl]benzonitrile to letrozole by a process according to any of claims 12.

27. A process according to claim 25, wherein the 4-(halomethyl)benzonitrile in step (a) is 4-(bromomethyl)benzonitrile, and the 4-halobenzonitrile in step (b) is 4-fluorobenzonitrile.

28. A process according to claim 25, wherein steps (a) and (b) are carried out in one pot without isolation of 4-[1-(1,2,4-triazolyl)methyl]benzonitrile.

29. A process according to claim 25, further comprising crystallizing the letrozole.

30. A process according to claim 29, wherein the letrozole is crystallized from a mixture of water and a water-miscible solvent.

31. The process according to claim 30, wherein the water-miscible solvent is selected from the group consisting of dimethylformamide, acetone, methylpyrrolidone, or dimethylacetamide, and mixtures thereof.

32. A process according to claim 25, further comprising decolorizing letrozole with activated charcoal in the presence of a reducing agent; wherein the reducing agent is sodium metabisulfite or a thiosulfate.

33. A process for decolorizing letrozole, comprising treating letrozole with activated charcoal in the presence of a reducing agent; wherein the reducing agent is sodium metabisulfite or a thiosulfate.

34. The process of claim 33, wherein the reducing agent is sodium metabisulfite.

35. A process for the preparation of letrozole,

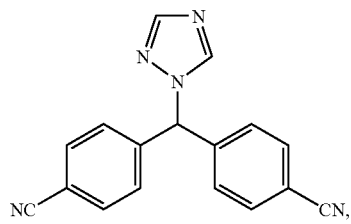

comprising reacting a 4-(halomethyl)benzonitrile with a salt of 1H-1,2,4-triazole to form 4-[1-(1,2,4-triazolyl)methyl]benzonitrile isolating the resulting 4-[1-(1,2,4-triazolyl)methyl]benzonitrile, combining the isolated 4-[1-(1,2,4-triazolyl)methyl]benzonitrile with a 4-halobenzonitrile, and adding a base selected from the group consisting of sodium bis(trimethylsilyl)amide, hexyl lithium, butyl lithium, lithium diisopropylamide, alkoxides, and mixtures thereof, forming letrozole.

36. A one-pot process for the preparation of letrozole,

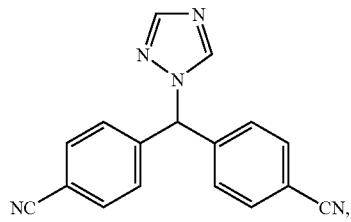

comprising reacting a 4-(halomethyl)benzonitrile with a salt of 1H-1,2,4-triazole to form 4-[1-(1,2,4-triazolyl)methyl]benzonitrile, combining the resulting 4-[1-(1,2,4-triazolyl)methyl]benzonitrile with a 4-halobenzonitrile, and adding a base selected from the group consisting of sodium bis(trimethylsilyl)amide, hexyl lithium, butyl lithium, lithium diisopropylamide, alkoxides, and mixtures thereof, forming letrozole, wherein the 4-[1-(1,2,4-triazolyl)methyl]benzonitrile with a 4-halobenzonitrile is not isolated prior to its reaction with the 4-halobenzonitrile.

37. The process according to claim 36, further comprising combining the resulting 4-[1-(1,2,4-triazolyl)methyl]benzonitrile with a 4-halobenzonitrile with a 4-halobenzonitrile in a solvent of dimethylacetamide, wherein the base is sodium bis(trimethylsilyl)amide.

38. The process according to claim 36, further comprising combining the resulting 4-[1-(1,2,4-triazolyl)methyl]benzonitrile with a 4-halobenzonitrile with a 4-halobenzonitrile in a solvent of dimethylformamide, wherein the base is a t-butoxide.

* * * * *

UNITED STATES PATENT AND TRADEMARK OFFICE
CERTIFICATE OF CORRECTION

PATENT NO. : 7,705,159 B2  Page 1 of 1
APPLICATION NO. : 11/482228
DATED : April 27, 2010
INVENTOR(S) : MacDonald et al.

It is certified that error appears in the above-identified patent and that said Letters Patent is hereby corrected as shown below:

Column 12
Line 62, change "K2CO3" to --$K_2CO_3$--

Column 18
Line 15, change "1H-1,2,4triazole"to --1H-1,2,4-triazole--
Line 22, change "4(iodomethyl)benzonitrile" to --4-(iodomethyl)benzonitrile--
Line 26, change "1H-1,2,4triazole" to --1H-1,2,4-triazole--
Lines 41-42, change "from 4-[1-(1,2,4-triazolyl)methyl]benzonitrile the in" to
--from the 4-[1-(1,2,4-triazolyl)methyl]benzonitrile in--

Column 19
Line 47, change "(1,2,4-triazoly)" to --(1,2,4-triazolyl)--
Line 50, change "(1,2,4-triazoly)" to --(1,2,4-triazolyl)--

Signed and Sealed this

Twenty-second Day of June, 2010

David J. Kappos
*Director of the United States Patent and Trademark Office*